United States Patent [19]
Levy et al.

[11] 3,966,919
[45] June 29, 1976

[54] O,O,O',O'-TETRAALKYL, O,O'-VINYLENEDI-p-PHENYLENE PHOSPHOROTHIOATES AND COMPOSITIONS CONTAINING THE SAME FOR THE CONTROL OF SIPHONAPTERA INFESTATIONS

[75] Inventors: Stephen David Levy, Trenton; Gordon Paul Poeschel, Kinnelon; Michael Stanley Schrider, South Bound Brook, all of N.J.

[73] Assignee: American Cyanamid Company, Stamford, Conn.

[22] Filed: Feb. 12, 1975

[21] Appl. No.: 549,220

Related U.S. Application Data

[63] Continuation-in-part of Ser. No. 460,257, April 11, 1974, Pat. No. 3,907,936.

[52] U.S. Cl.................................. 424/206; 260/930
[51] Int. Cl.².......................................... A01N 9/36
[58] Field of Search...................... 260/930; 424/206

[56] References Cited
UNITED STATES PATENTS

| | | | |
|---|---|---|---|
| 2,922,812 | 1/1960 | Gilbert et al........................ | 424/206 |
| 3,459,856 | 8/1969 | Lovell et al.......................... | 424/206 |

*Primary Examiner*—V. D. Turner
*Attorney, Agent, or Firm*—Denis A. Polyn

[57] ABSTRACT

Method of using O,O,O',O'-tetraalkyl($C_1$–$C_4$)-O,O'-vinylenedi-p-phenylene phosphorothioates for the control of siphonaptera infestations and compositions containing said phosphorothioates as the active component, are described.

12 Claims, No Drawings

O,O,O',O'-TETRAALKYL, O,O'-VINYLENEDI-P-PHENYLENE PHOSPHOROTHIOATES AND COMPOSITIONS CONTAINING THE SAME FOR THE CONTROL OF SIPHONAPTERA INFESTATIONS

This application is a continuation-in-part of application Ser. No. 460,257 filed Apr. 11, 1974, now U.S. Pat. No. 3,907,936.

DESCRIPTION OF THE INVENTION

The present invention relates to a method of using compounds of the formula:

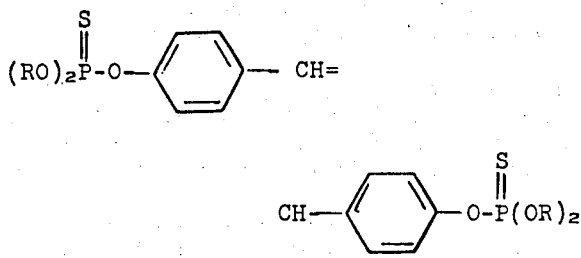

wherein R is $C_1$–$C_4$ alkyl, such as methyl, ethyl, propyl, isopropyl, butyl or isobutyl, and to compositions containing said esters as the active ingredient for controlling Siphonaptera infestations.

The compounds of the above formula may be prepared by reacting 4,4'-dihydroxystilbene with an O,O-di(alkyl $C_1$–$C_4$)-thiophosphoryl halide. The reaction may be illustrated as follows:

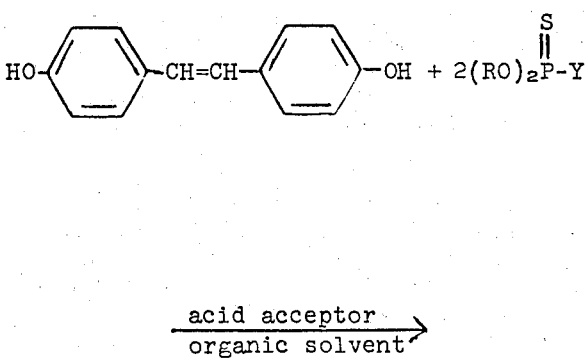

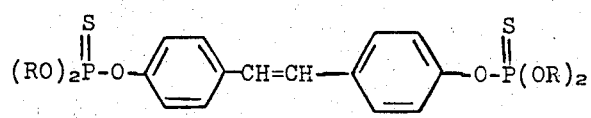

wherein Y is halogen, such as chloro or bromo, and R is $C_1$–$C_4$ alkyl.

The starting materials are well known. Thus, the 4,4'-dihydroxystilbene is a mixture of cis and trans isomers usually with the trans isomer predominating, obtainable by several procedures according to Beilstein Organische Chemie Band VI, pg. 1022. The isomers can be separated by methods well known in the Chemical Arts and when the pure isomer is used in the reaction, the corresponding isomeric form will be obtained in the final product. The dialkyl thiophosphoryl halides are described in a multiplicity of references. The reaction is conducted in an organic solvent such as, for example, the oxygenated solvents t-butyl alcohol, methyl isobutyl ketone, acetone, methyl ethyl ketone or diethyl ether, hydrocarbon solvents such as benzene, toluene, xylene or chloroform, and the like, in the presence of an acid acceptor such as, for example, potassium t-butyl alkoxide, sodium methoxide, sodium hydroxide, sodium carbonate, pyridine, triethylamine, and the like. The reaction may also be conducted in the absence of an acid-acceptor if conditions are such that the acid released by the reaction is efficiently removed as by distillation.

A satisfactory production of the above-described compounds are obtained when the molar ratio of dihydroxystilbene to dialkyl thiophosphoryl halide to base is about 1:2:2 and the reaction is carried out at a temperature from 40°C. to 100°C. Other methods for preparing the above compounds involving the same intermediates are also known.

The compounds of this invention have been found to by highly siphonaptericidal and effective against *Ctenocephalides spp.* and are useful in controlling flea infestations of domestic warm-blooded animals, particularly cats and dogs.

When the active components of this invention are used as control agents for Siphonaptera in insecticidal and larvicidal amounts, such components may be brought into contact with adult insects, or larvae of said insects, or they may be applied to the habitat, breeding grounds and/or dietary media of said insects or larvae, that is organic matter, living or dead, which forms their food, or to the animal host of the insects.

It is a good practice to formulate the active components of this invention with a conventional solid or liquid diluent and a formulation aid. As siphonaptericides they may be formulated as granulars, dusts, dust concentrates, wettable powders, emulsifiable concentrates, and the like. They may also be incorporated in baits for adult fleas or they may be incorporated in a plastic such as a polyvinyl chloride, and made up in the form of a collar and placed around the neck of an animal.

Useful liquid diluents in which the components of this invention may be dissolved or suspended include, for example, water, xylene, benzene, keto alcohols such as diacetone alcohol, lower alcohols $C_1$–$C_4$, fuel oil, esters and the like, either with or without a surfactant. For application, the resulting solution or suspension can be further diluted with either water or an organic diluent, such as deodorized kerosene. Concentrations in the range from 5% to 95% active ingredient by weight are generally suitable for the initial solution or suspension. When diluted for application, suitable solutions and suspensions contain the active ingredient in concentrations from 1 to about 90% by weight.

The term "suspension," as employed herein, includes dispersions of either solid particles or immiscible liquid droplets. The latter type of dispersion is more particularly referred to when fully dispersed as an emulsion.

In the preparation of a dispersion of solid particles, is is preferable to include a dispersing agent to promote the separation or deflocculation of the particles of the active component. Examples of such dispersing agents are sodium lignosulfonate, calcium lignosulfonate, the sodium salt of a naphthalenesulfonic acid condensed with formaldehyde, the sodium salts of polymeric carboxylic acids, the sodium salts of carboxylated polyelectrolytes, and the like.

Dusts or dust concentrates, can be prepared by grinding together an inert solid diluent such as attapulgite, kaolin, walnut shell flour, diatomaceous earth, ground corn cob grits, or ground coconut shell, and the active ingredient, where such active ingredient is in solid form. Where the active ingredient is a liquid, it may be sprayed on the carrier and thoroughly mixed with it or it may be dissolved in a solvent such as acetone or xylene, and the solution sprayed on the solid carrier. Dusts usually contain from about 1 to 15% by weight of active ingredient, whereas concentrates may contain from about 16 to about 85% by weight of the active material.

Wettable powders are prepared in the same fashion as dust concentrates, excepting that they contain from 50 to 90% active component and about 10 to 20% by weight of a wetting agent and 5 to 10% by weight of a dispersing agent are included. Examples of such wetting agents are polyoxyethylene derivatives, sodium N-methyl-N-oleoyl taurate, alkyl phenoxy polyoxyethylene ethanol, and the like.

It is obvious that dusts can also be prepared from wettable powders. For example, to prepare a 10% dust, 20% by weight of a 50% wettable powder can be blended with about 80% by weight of a solid carrier, such as kaolin. Suitable equipment for such preparations are ribbon-type blenders and double-cone blenders. It is also obvious that the concentration of active ingredient in such dust formulations can readily be varied by adjusting the amount of wettable powder and carrier used. Such dusts will generally vary between about 1 to 15% by weight of active ingredient, although higher or lower concentrations may also be prepared. permitted It A granular formulation can be prepared by blending a small amount, i.e., about 0.3% by weight, of a fused collodial silica with about 5.6% by weight of the active ingredient and airmilling the mixture to a uniform blend. Silica sand, about 85.7% by weight, is then placed in a blender along with about 0.7% by weight of calcium-sodium lignin sulfonate powder and 4.2% of a 1% aqueous solution of calcium-sodium lignin sulfonate. The mixture is blended and then 3.5% by weight of synthetic calcium silicate is added. The mixture is premitted to continue blending for several minutes until the finished product is uniformly coated and free flowing. it is, of course, obvious that the amount of active ingredient in the formulated granular product can be widely varied. This simply requires appropriate adjustment of the amount of granular carrier used and/or adjuvants added. It is likewise obvious that sorptive granular carriers, as well as nonsorptive carriers, can be employed in the preparation of the granular formulations.

The active components of the present invention may also be prepared as emulsifiable concentrates by dissolving or dispersing about 10 to 75% by weight of the active component in a suitable solvent or carrier such as a petroleum distillate having a minimum aromatic content of 85% and admixing therewith about 10% by weight of an emulsifier such as polyoxyethylene derivatives and blends with alkyl aryl sulfonates. These concentrates are also generally dispersed in water or other suitable solvent for application.

The application of the active components of this invention in the form of an emulsion of the oil-in-water type, or of the water-in-oil (invert) type may also be carried out. The preferred oil-in-water type may be formed by slowly admixing an emulsifiable concentrate with water containing an emulsifying agent.

Wettable powders and emulsifiable concentrates are particularly useful since they can be diluted with water and applied as dilute liquid sprays to an infested area, for which protection is sought, or they may be sprayed on or applied topically as by pour-on to animals which are to be protected from attack. In the latter situation the dilute liquid formulation may also be applied by dipping.

Field application of the active components of this invention to animals and infested areas, may be made by conventional equipment, such as power dusters, boom and hand sprayers, spray dusters, spray races and the like.

In the practice of this invention control of Siphonaptera can be effected by thoroughly spraying an infested animal with an aqueous dispersion containing from 0.1% active ingredient w/v to 10.0% active ingredient w/v 0.1% active ingredient w/v contains 1.0 gram of active ingredient per liter; each animal is sprayed with from 10 ml. to 200 ml. of solution.

Preferentially, application to dogs and cats to control fleas can be effected by spraying each animal with aqueous solutions containing from 0.355% to 10% (w/v) active ingredient to provide from 1.25 milligrams to 40 milligrams of active material per kilogram of body weight.

Application to dogs and cats to control fleas can also be effected by treating each animal with a dust containing about 2% active ingredient to provide from 10 milligrams to 120 milligrams of active ingredient per kilogram of body weight.

SPECIFIC DISCLOSURE

In order that the present invention may be more fully understood, the following examples are given primarily by way of illustration. No specific details or enumerations contained therein should be construed as limitations on the present invention, except insofar as they appear in the claims. All parts and percentages are by weight unless otherwise specifically designated.

EXAMPLE 1

Preparation of O,O,O′,O′-Tetramethyl O,O′-vinylenedi-p-phenylene phosphorothioate 10.6 Grams (0.05 mole) of 4,4′-dihydroxystilbene is slurried in 150 ml. of tertiary butyl alcohol at 70°C. and 17.66 grams (0.11 mole) of O,O-dimethylphosphorochloridothioate is added thereto. An amount of 11.2 grams (0.10 mole) of potassium tertiary butyl alcoholate in 100 ml. of tertiary butyl alcohol is added to the reaction mixture and the temperature is raised to 75°C. The reaction mixture is held at 75°C. for 15 minutes and then concentrated to obtain a residue which is dissolved in 250 ml. of diethyl ether. The ethereal solution is extracted successively with water, 5% aqueous potassium hydroxide, dilute hydrochloric acid and water saturated with sodium chloride. The ethereal solution is then concentrated to obtain 18.9 grams of a white solid which on recrystallization from 250 mls. of boiling isopropyl alcohol yields 12.4 grams of white solid, melting point 112°–113°C. This material is then slurried in 200 ml. of hexane and heated to reflux. About 80 ml. of benzene are slowly added to dissolve any insolubles and the solution is filtered and then cooled to room temperature. The precipitate is separated by filtration and dried to obtain 10.1 grams of material, melting point 113.5°–114°C., which is homogeneous by thin layer chromatography. Analysis calculated for $C_{18}H_{22}O_6P_2S_2$ (in %): C, 46.95; H, 4.82; P, 13.45; S, 13.93. Found: C, 47.16; H, 4.96; P, 13.64; S, 14.04.

Employing the same procedure and substituting O,O-diethylphosporochloridothioate for O,O-dimethyl phosphorochloridothioate yields 0,0,0',0'-tetraethyl 0,0'-vinylenedi-p-phenylene phosphorothioate.

Similarly, substituting O,O-dipropyl phosphorochloridate O,O-diisopropyl phosphorochloridothioate for O,O-dimethyl phosphorochloridothioate yields the corresponding 0,0,0',0'-tetrapropyl 0,0'-vinylenedi-p-phenylene phosphate and 0,0,0',0'-tetraisopropyl 0,0'-vinylenedi-p-phenylenephosphorothioate.

Using as starting material trans 4,4'-dihydroxystilbene or cis 4,4'-dihydroxystilbene, the corresponding trans or cis product of the invention is obtained.

EXAMPLE 2

Siphonaptericidal Activity

The siphonaptericidal efficacy of the compounds of this invention is demonstrated by the following test wherein 0,0,0',0'-tetramethyl 0,0'-vinylenedi-p-phenylene phosphorothioate is utilized as the active ingredient. In this test ten adult fleas of the species *Ctenocephalides felis* are sprayed for 30 seconds with an acetone/water solution containing 1.0 ppm. of the test compound. After this treatment, the fleas are maintained for 48 hours at room temperature and 80+% relative humidity. At the end of this period, the fleas are examined and mortality counts made. With the above-named composition, which is representative of the compounds disclosed, 100 percent mortality is obtained.

What is claimed is:

1. A composition useful in controlling infestations of a domestic warm-blooded animal with Siphonaptera which comprises from 1 to about 90% of a compound of the formula:

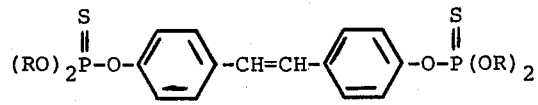

wherein each R is the same and is $C_1$–$C_4$ alkyl in association with a carrier.

2. The composition according to claim 1 comprising a dust containing from 1 to 15% by weight of the compound and a diluent.

3. The composition according to claim 1 comprising a wettable powder containing from 50 to 90% by weight of the compound and from 10 to 20% by weight of a wetting agent and from 5 to 10% by weight of a dispersing agent.

4. The composition according to claim 1 comprising an emulsifiable concentrate containing from 10 to 75% by weight of the compound and an effective amount of an emulsifying agent.

5. The composition according to claim 1 comprising a dispersion containing from 0.1 to 10.0% by weight of the compound and an effective amount of a dispersing agent.

6. A composition useful in controlling infestations of a cat or dog with Siphonaptera which comprises from 1 to about 90% of a compound of the formula:

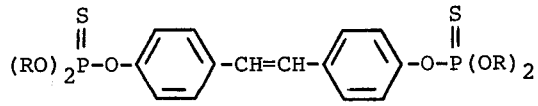

wherein each R is the same and is $C_1$–$C_4$ alkyl in association with a carrier.

7. A method of controlling Ctenocephalides infestations on a domestic warm-blooded animal comprising contacting said Ctenocephalides with a toxically effective amount of a compound of the formula:

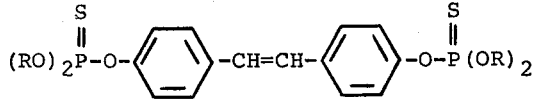

wherein each R is the same and is $C_1$–$C_4$ alkyl.

8. The method according to claim 7 wherein the active ingredient is the compound in which R is methyl.

9. The method according to claim 7 wherein the active component is a compound of the formula:

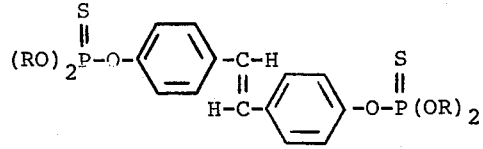

wherein each R is the same and is $C_1$–$C_4$ alkyl.

10. The method according to claim 7 wherein the active component is a compound of the formula:

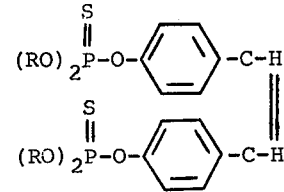

wherein each R is the same and is $C_1$–$C_4$ alkyl.

11. The method according to claim 7 wherein the active component is a compound of the formula:

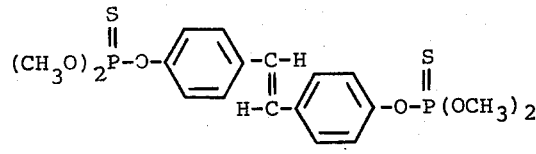

12. A method according to claim 7 wherein the active component is a compound of the formula:

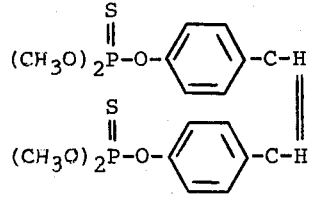

* * * * *